United States Patent [19]

Hutson, Jr.

[11] 4,371,718
[45] Feb. 1, 1983

[54] USING BUTENES TO FRACTIONATE METHANOL FROM METHYL-TERTIARY-BUTYL ETHER

[75] Inventor: Thomas Hutson, Jr., Bartlesville, Okla.

[73] Assignee: Phillips Petroleum Company, Bartlesville, Okla.

[21] Appl. No.: 279,916

[22] Filed: Jul. 2, 1981

[51] Int. Cl.³ .................. B01D 3/36; C07C 41/42
[52] U.S. Cl. .................. 568/697; 203/3; 203/41; 203/70; 203/DIG. 23; 568/699
[58] Field of Search .................. 568/699, 697, 917; 203/70, 3, 41, DIG. 23; 585/820, 822, 823, 824, 826

[56] References Cited

U.S. PATENT DOCUMENTS

| | | | |
|---|---|---|---|
| 2,367,701 | 1/1945 | Tooke | 203/43 |
| 2,368,050 | 1/1945 | Tooke | 203/46 |
| 2,440,784 | 5/1948 | Perdew | 208/188 |
| 2,480,940 | 9/1949 | Leum et al. | 568/697 |
| 2,619,497 | 11/1952 | Hockberger | 568/917 |
| 2,621,203 | 12/1952 | Cope | 568/917 |
| 2,647,150 | 7/1953 | Askerold | 568/917 |
| 2,826,615 | 3/1958 | Campbell | 568/917 |
| 2,880,144 | 3/1959 | Bush | 203/44 |
| 3,021,374 | 2/1962 | Radzitzky | 568/917 |
| 3,119,766 | 1/1964 | Voltz et al. | 208/291 |
| 3,485,879 | 12/1969 | Mameniskis et al. | 568/917 |
| 3,616,267 | 10/1971 | McNeil | 203/3 |
| 3,846,088 | 11/1974 | Brown et al. | 568/697 X |
| 3,940,450 | 2/1976 | Lee | 568/697 |
| 3,979,461 | 9/1976 | Ancillotti et al. | 568/697 |
| 4,008,289 | 2/1977 | Ward et al. | 203/41 |
| 4,039,590 | 8/1977 | Ancillotti et al. | 568/697 |
| 4,090,885 | 5/1978 | Lyons | 568/671 X |
| 4,144,138 | 3/1979 | Rao et al. | 203/46 |
| 4,198,530 | 4/1980 | Wentzheimer et al. | 568/699 |
| 4,256,465 | 3/1981 | Takezono et al. | 568/697 X |
| 4,282,389 | 8/1981 | Droste et al. | 203/75 |
| 4,299,999 | 11/1981 | Mikitenko et al. | 203/70 |
| 4,302,298 | 11/1981 | Mikitenko et al. | 203/94 |

FOREIGN PATENT DOCUMENTS 883081 of 0000 Belgium .

OTHER PUBLICATIONS

Obenaus and Droste, "The New and Versatile Hule—Process to Produce the Octane Improving MTB", AICHE Mtg. in Phil., (1977/78), pp. 1-22.
A. Clementi et al., "Upgrade C₄'S With MTBE Process", Hydrocarbon Processing, Dec., 1979, pp. 109-113.
J. D. Chase et al., "MTBE and TAME—a good octane boosting combo", The Oil and Gas Journal, Apr. 9, 1979, pp. 149-152.

Primary Examiner—Wilbur L. Bascomb, Jr.

[57] ABSTRACT

Butenes are added to the methanol-containing methyl-tertiary-butyl ether (MTBE) reactor effluent fractionation to effect recovery of substantially methanol-free MTBE bottoms product. Methanol analysis taken below the fractionator feed locus manipulates control of butenes addition. In an embodiment, the methanol-butenes-containing overhead stream from the fractionation is treated over activated alumina to adsorb methanol, yielding a methanol-free butenes feed for HF alkylation of isobutane. The used adsorbent can be regenerated using hot butenes product and/or MTBE reactor feed vapor with the recovered methanol being recycled to the MTBE reaction.

7 Claims, 1 Drawing Figure

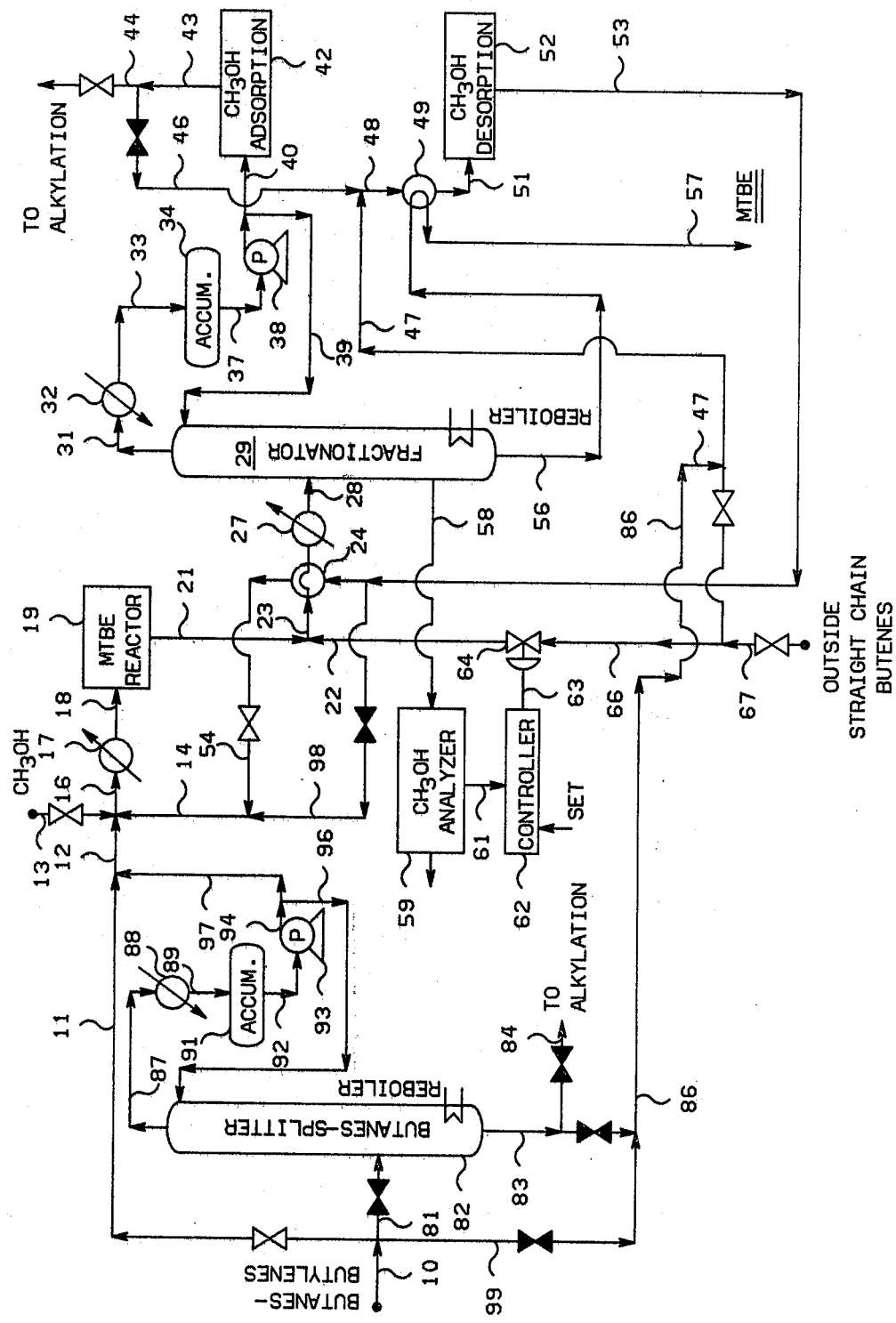

USING BUTENES TO FRACTIONATE METHANOL FROM METHYL-TERTIARY-BUTYL ETHER

FIELD OF THE INVENTION

The invention pertains to a process for the production of methyl-tertiary-butyl ether. In another aspect, the invention relates to a process utilizing butenes to fractionate methanol from the methanol-tertiary-butyl ether product stream. In another aspect, the invention pertains to a method to cover methanol from a fractionated butenes stream.

BACKGROUND OF THE INVENTION

Methyl-tertiary-butyl ether (MTBE) is well recognized as a suitable blending stock for raising octane of gasoline. The product has been in use for some time in Europe as a blending component with gasoline, and the usage of MTBE in the United States is increasing. MTBE and related ethers, blended into gasoline at a 10 to 20 percent level, increase both motor and research octane numbers by several units. The Environmental Protection Agency has sanctioned the use of MTBE in concentrations up to about 7 liquid volume percent in the United States. Due to limitations in the amount of raw material available (isobutylenes) in the United States for use in making MTBE, the U.S. gasoline pool probably will not contain more than about 3 percent at most for the time being. Nevertheless, even this is a desirable supplement to the total gasoline available.

Addition of even up to 10 percent of such ether to gasoline reportedly does not significantly affect any properties of the resulting blend except increasing octane.

MTBE is produced by reacting isobutylene with methanol, resulting in the formation of methyl-tertiary-butyl ether. The reaction normally is conducted in liquid phase and relatively mild conditions. While mixed butylene streams can be employed, only the tertiary olefin, isobutylene, reacts at the conditions employed. A catalyst normally is used, an ion exchange resin. The isobutylene component can be obtained from various sources, such as naphtha cracking, catalytic cracking, and so on. Refer *Hydrocarbon Processing*, December, 1979, pages 109 and following; and *The Oil and Gas Journal*, Apr. 9, 1979, pages 149 and following.

BRIEF DESCRIPTION OF THE INVENTION

Butenes are added to the methanol-containing methyl-tertiary-butyl ether (MTBE) reactor effluent fractionation to effect recovery of substantially methanol-free MTBE bottoms product. Methanol analysis taken below the fractionator feed locus manipulates control of butenes addition. In an embodiment, the methanol-butenes-containing overhead stream from the fractionation is treated over activated alumina to adsorb methanol, yielding a methanol-free butenes feed for HF alkylation of isobutane. The used adsorbent can be regenerated using hot butenes product and/or MTBE reactor feed vapor with the recovered methanol being recycled to the MTBE reaction.

BRIEF DESCRIPTION OF THE DRAWING

A mixed stream 10 of butanes/butylenes is fed 11, 12 to admixture with methanol 13 to form stream 16, 18, to methyl-tertiary-butyl ether reactor 19. The resulting reactor effluent 21 then is admixed as necessary with straight-chain butenes 67 for feed to fractionator 29. Fractionator 29 provides overhead vapor comprising isobutane, normal butane, added and residual butylenes, and any unreacted methanol overhead 31 for recycle, treatment, absorption of methanol 42 for recovery and recycle, etc. Bottoms 56 from fractionator 29 is a stream of substantially pure methyl-tertiary-butyl ether. Other details of the drawing will be described hereinafter in the detailed description of the invention.

REACTION OF ISOBUTYLENE WITH METHANOL

A process for the production of MTBE is disclosed in some detail in an article entitled "The New and Versatile Hule-Process to Product the Octane improving MTB" authored by Dr. Fritz Obenaus and Dr. Wilhelm Droste of Chemische Werke Huls AG, West Germany, in a manuscript available from the American Institute of Chemical Engineers, Philadelphia (1978).

The conversion of the isobutylenes in a mixed butene stream to methyl-tertiary-butyl ether by reaction with methanol can be carried out in any suitable manner known in the art.

The reaction of the isobutylene with methanol can be carried out under any suitable reaction conditions. The mole ratio of methanol to isobutylene generally is in the range of about 0.05 to 10, more usually about 0.1 to 5, and still more usually about 1 to 1, at a temperature in the range of about 60° F. to 300° F., more usually about 120° F. to 200° F., employing a pressure sufficient to maintain the reactants sufficiently in the liquid stage, typically in the range of about 30 psig to 300 psig.

The reaction usually employs an acid type ion exchange resin, such as a high molecular weight carbonaceous material containing sulfonate groups —$SO_3H$. Sulfonated resins of various types are widely available under various commercial names, and of various types such as the sulfonated coals, phenol formaldehyde resins reactive with sulfuric acid, sulfonated resinous polymers of cumarone-indene with cyclopentadiene, various commercially available strongly acidic cationic exchange resins such as sulfonated polystyrene resins, and various others. The catalyst is employed in a finely divided state of a mesh size of such as about 10 to 50 U.S. sieve, employing the catalyst in a particulate solid form in the stirred liquid reaction system, employing about 0.5 to 50 percent dry weight catalyst relative to liquid content of the reactor.

Preferably, a fixed bed of particulate solid ion exchange resin catalyst, e.g. such as Amberlyst 15, is employed in a reactor to effect production of MTBE from methanol and isobutylene. Temperatures used can range from about 100° F. to 250° F., more preferably about 120° F. to 200° F., at a pressure sufficient to maintain liquid phase. Liquid hourly space velocity, volumes of feed per volume of catalyst per hour, preferably is about 5 to 35.

The effluent from the reaction zone comprises isobutane, normal butane, straight-chain butylene, a small amount of unreacted isobutylene, a small amount of unreacted methanol, and product methyl-tertiary-butyl ether. This then is subjected to a separatory procedure in accordance with my invention for recovery of the methyl-tertiary-butyl ether in surprisingly pure form, as well as separation and recovery of the unreacted methanol.

OPERATING CONDITIONS

As is known to those skilled in the arts of fractionation, MTBE manufacture, and adsorption, various temperature:pressure:reflux ratios, reactant ratios, and space velocities combinations can be selected to effect the desire operational result.

Suggested conditions are shown below. The numbers to the left referring to streams shown on my FIGURE attached.

| (19) MTBE Reactor: | |
|---|---|
| Temperature, °F. | 125 |
| Pressure, psig | to effect liquid |
| Isobutylene/Methanol Mol Ratio | ~1:1 |
| Conversion, Vol. % | ~96 |
| Catalyst | |
| Amberlyst 15 | |
| (Rohm-Haas) | |
| Liquid Hourly Space Velocity | 5 |
| (Volume Feed/Vol. Cat./Hour) | |
| Total Volume Percent of Feed of | |
| Isobutylene and Methanol | 27.84 |
| (29) Fractionator: | |
| Pressure, psia | 80 |
| Temperatures, °F. | |
| Top | 122° F. |
| Bottom | 236° F. |
| (42) Adsorption Operating (Liquid): | |
| Temperature, °F. | 85 |
| Pressure, psia | 40 |
| Adsorbent: | |
| Activated Alumina | |
| Liquid Hourly Space Velocity | 0.5 |
| (Volume Feed/Vol. Adsorbent/hour) | |
| (52) Desorption Conditions (Vapor): | |
| Temperature, °F. | 350 |
| Pressure, psia | 250 |
| Vapor Hourly Space Velocity | 15 |
| (Volume Desorbent/Volume Adsorbent/hr. | |

The straight-chain butenes (butylenes) can be provided by an outside feed of straight-chain butenes, or can be obtained by the original feed into the system of a mixed butylenes stream containing straight-chain butenes, some of which in part can be utilized for feed to the fractionator to assist in removing methanol from the MTBE reactor stream, and some can be utilized for methanol desorption and recycle back to the MTBE reactor.

Importantly, in feeding the straight-chain butylenes to the fractionator, the straight-chain butylenes effect azeotropic distillation of methanol from the methanol containing MTBE reactor stream. This is important, since it gives a clean stripping of methanol from the MTBE effluent in the fractionator, producing an unusually pure MTBE bottom stream from the fractionator.

| Methanol-Butene-1 Azeotropic Distillation at 125° F. | |
|---|---|
| Pressure, mm Hg (abs) | Wt. % Butene-1 in Vapor |
| 1443 | 95.7 |
| 4652 | 96.7 |
| 4765 | 96.7 |

DETAILED DESCRIPTION OF THE DRAWING

Butanes-butylenes stream 10, comprising reactant isobutylene, is passed via conduits 11 and 12 and is admixed with reactant methanol 13 and a recycle methanol stream 14 from regeneration of a methanol adsorption described hereinbelow, and the mass is passed via conduit 16, is heated in indirect heat exchanger 17, and is passed via conduit 18 to methyl tertiary butyl ether reaction zone 19.

Effluent 21 from zone 19 (comprising isobutane, normal butane, straight chain butylenes, a small amount of unreacted isobutylene, a small amount of unreacted methanol, and product methyl tertiary butyl ether) is admixed with straight chain butylenes as needed from conduit 22, this addition of straight chain butylenes described hereinbelow, and the mass is passed via conduit 23, indirect heater 24, and conduit 28 to fractionator 29.

Overhead vapor stream 31 (comprising isobutane, normal butane, straight chain butylenes, the small amount of unreacted isobutylene, and the small amount of unreacted methanol) is condensed in indirect heat exchanger 32 and is passed via conduit 33 to overhead accumulator 34. Liquid is passed from accumulator 34 via conduit 37, pump 38, and conduit 39 as reflux for fractionator 29. Yield liquid 40 is charged to methanol adsorption zone 42 containing activated alumina. Yield 43 from adsorption zone 42 is passed at least in part via conduit 44 to such as HF alkylation, and, at least in part, can be passed via conduit 46 along with outside straight chain butylenes, as needed, through indirect heating means 49 and via conduit 51 to desorb methanol from methanol adsorption zone 52 on the desorption cycle. Effluent 53 from zone 52 (containing the methanol recovered from overhead yield 40 of fractionator 29, is passed via indirect heat exchanger 24 and via conduits 54, 14, 16, heat exchanger 17, and conduit 18 to methyl tertiary butyl ether reaction zone 19. Temperature modification of stream 53 can be effected by, when needed, by-passing a part of stream 53 by way of conduit 98 and then to conduit 14. Stream 56 from fractionator 29 (MTBE product free of methanol) is passed via indirect heat exchanger 49 and is recovered as product via conduit 57, for use as motor fuel additive.

Sample stream 58 from fractionator 29, removed at a locus below feed stream 28 and above the reboiler and MTBE bottoms product removal 56 is passed to methanol analysis unit 59 wherefrom a signal 61, representative of the methanol content in fractionator 29 at the stream 58 removal locus, is passed to controller 62. The output 63 from controller 62 manipulates valve 64 (can be flow controller, flow measurement means, and valve, conventionally used) which valve 64 controls the addition of straight chain butylenes to fractionator 29 via conduits 67, 66, 22, and 23, heat exchangers 24 and 27, and conduit 28, the straight chain butylenes effecting removal of methanol in conduit 28 charged to fractionator 29 in the overhead product 31, eliminating passage of methanol out the bottom with MTBE removed at 56. Straight chain butylenes effect azeotropic distillation of methanol from the methanol-containing mixture.

Optionally, feed 10, at least in part, can be via conduit 81 charged to a conventionally operated butanes splitter 82. Overhead vapor 87 from splitter 82, comprising isobutane, isobutylene, and butene-1, is condensed in heat exchanger 88 and passed via conduit 89 to overhead accumulator 91. Liquid 92 from accumulator 91 is pumped 93 and, in part, passed via conduits 94 and 96 as reflux for splitter 82. The yield liquid is passed via 97 to conduit 12 and onto MTBE reactor 19. Bottoms 83 from splitter 82 can be passed via conduit 84 to an alkylation and/or passed via line 86 to conduits 47 and 48 for use as desorption fluid for zone 52. Also, a part of feed 10 can be passed via conduit 99 to conduit 86 and ultimately used as, at least, a part of the desorption fluid for zone 52.

Zones 42 and 52 represent adsorption zones for methanol. Several zones can be used, part of the zones on adsorption and part of the zones on desorption.

CALCULATED EXAMPLE

The following data are presented in order to further understand the scope of my invention. Particular streams and relationships are intended to be illustrative, and not limitative of the reasonable scope of my invention. It is recognized, for example, that a feed stream of mixed butylenes can vary widely in composition, such as disclosed in the articles hereinbefore mentioned in this my specification. Certainly ratios of methanol to isobutylene can vary widely, since excess over stoichiometric amounts of either one can be readily removed from the resulting feedstream in accordance with my invention.

| | Calculated Typical Operation | | | |
|---|---|---|---|---|
| (10) | Feed Stream: | | | |
| | Barrels/hour | | 475.00 | |
| | Composition, Vol. % | | | |
| | Isobutane | 21.93% | | |
| | Isobutylene | 21.05% | | |
| | Butene-1 | 13.16% | $\frac{43.86 \times 475}{100}$ | = 208.33 B/H |
| | Butene-2 | 30.70% | | |
| | Normal Butane | 13.16% | | |
| | Total | 100.00% | | |
| (12) | Is feedstream (10), above | | | |
| (13) | Methanol: | | | |
| | Barrels/hour | | 43.04 | |
| (14) | Recycled Methanol from (52): (Desorp.) | | | |
| | Barrels/hour | | 68.80 Total | |
| | Composition, Vol. % | B/H | | |
| | Methanol | 17.20 | 25.0% | |
| | Hydrocarbons | 51.60 | 75.0% | |
| | Total | 68.80 | 100.00% | |
| (18) | Blend of Streams (12), (13) and (14): | | | |
| (21) | MTBE Reactor Product: | | | |
| | Barrels/hour | | 568.95 | |
| | Composition, Vol. % | BPH | Vol. % | |
| | Methanol | 17.20 | 3.02 | |
| | Isobutylene | 4.00 | 0.70 | |
| | Isobutane | 104.17 | 18.31 | |
| | Normal Butenes | 259.93 | 45.69 | (208.33 + 51.6) |
| | Normal Butane | 62.50 | 10.99 | |
| | MTBE | 121.15 | 21.29 | |
| | | 568.95 | 100.00 | |
| (66) | Straight Chain Butylenes: | | | |
| | Barrels/hour | | 175.50 | |
| | (99 volume percent butene-1 and butenes-2) | | | |
| (28) | Blend of Streams (21) and (66): | | | |
| (40) | Overhead Yield from (29): [21+66−MTBE] | | | |
| | Barrels/hour | | 623.30 | |
| | Composition, Vol. % | B/H | Vol. % | |
| | Methanol | 17.20 | 2.76% | |
| | Isobutylene | 4.00 | 0.64% | |
| | Isobutane | 104.17 | 16.71% | |
| | Normal Butenes | 435.43 | 69.86% (a) | (259.93 + |
| | Normal Butane | 62.5 | 10.03% | 175.5) |
| | | 623.3 | 100.00% | |

(a) Includes straight chain butenes added via conduit 66 to insure methanol is removed via conduit 31 from fractionator 29.

| (43) | Yield from Zone 42: | | | |
|---|---|---|---|---|
| | Barrels/hour | | 606.10 | |
| | Composition, Vol. % | B/H | Vol. % | |
| | Methanol | — | None | |
| | Isobutylene | 4.00 | 0.66% | |

| | Calculated Typical Operation | | |
|---|---|---|---|
| | Isobutane | 104.17 | 17.19% |
| | Normal Butenes | 435.43 | 71.84% |
| | Normal Butane | 62.50 | 10.31% |
| | | 606.1 | 100.00% |
| (47) | Desorption Fluid for (52): | | |
| | Barrels/hour (as liquid) | | 51.6 |
| | Composition, Vol. % | | |
| | (same as stream 66, above) | | |
| (53) | Yield from (52): | | |
| | (Same as Stream 14, above) | | |

The disclosure, including data, has illustrated the value and effectiveness of my invention. The knowledge and background of the field of the invention, of general principles of the chemical engineering and of other applicable sciences, and the exemplary data presented, have formed the bases to which the broad description of the invention, including the ranges of condition have been developed, and all formed the bases for my claims here appended.

I claim:

1. A process for the production of a substantially pure MTBE stream which comprises:
    (a) feeding methanol and isobutene to an MTBE reactor means,
    (b) reacting in said MTBE reactor means methanol with isobutene under reaction conditions under liquid phase conditions employing an ion exchange resin catalyst, thereby producing a reaction stream comprising unreacted methanol, unreacted isobutene, and MTBE,
    (c) feeding added n-butenes to a fractionation means,
    (d) feeding said reaction stream to said fractionation means,
    (e) fractionating in fractionating means said reaction stream with said added n-butenes, and taking an overhead vapor stream comprising unreacted isobutene and an azeotrope of said n-butenes with said unreacted methanol, wherein said n-butenes are present in an amount effective to take unreacted methanol overhead as an azeotrope, thereby producing substantially pure MTBE as liquid bottoms,
    (f) withdrawing a sample stream from said fractionation means said sample stream taken from said fractionation means below the input of said reaction stream and above the outlet of said bottoms stream,
    (g) monitoring the methanol content of said sample stream and generating a signal in response to the methanol content thereof,
    (h) controlling the addition of said added n-butenes in said step (c) to said fractionation means in response to said signal, whereby said signal controls the increase or decrease of addition of said added n-butenes, thereby maintaining an effective level of said n-butenes in said fractionation means to maintain substantially methanol-free bottoms.

2. The process according to claim 1 wherein said isobutene to said step (a) is an isobutene-containing stream further comprising butanes, n-butenes, and isobutene; said reacting in said step (b) is in the presence of said butanes; said reaction stream further contains butanes; said overhead from said step (e) further contains butanes; said overhead is condensed to provide a liquid stream, said liquid stream is subjected to adsorption by activated alumina, thereby adsorbing said methanol therefrom, and thereby producing a demethanolized stream comprising said butanes, n-butenes, and isobutene.

3. The process according to claim 2, further comprising desorbing said adsorped methanol with n-butenes, thereby forming a methanol/n-butenes stream, and recycling said methanol/n-butenes stream in admixture with an isobutene stream and a methanol stream to said step (a) to form additional methyl-tertiary-butyl ether in step (b).

4. The process according to claim 2 further comprising employing a portion of the isobutene stream for desorbing said adsorbed methanol, thereby producing a mixed stream of desorbed recovered methanol and desorbing isobutene, and employing said mixed stream of methanol/isobutene in said step (a) as at least a portion of said methanol and isobutene to said reacting step (b).

5. The process according to claim 2 further comprising:

(i) feeding at least a portion of a stream of admixed butanes/butenes to a splitter, splitting said stream, thereby producing a second overhead stream of isobutane, isobutene, and butene-1, and a bottoms stream comprising n-butane and butenes-2, employing said second overhead as said feeding (a) as at least a portion of said isobutene to said MTBE reactor means.

6. The process according to claim 5 further comprising employing a portion of said n-butane and butenes-2 from said splitter bottoms in desorption of said adsorbed methanol, and recycling the resulting desorbed methanol to said step (a) as at least a portion of said methanol to said MTBE reaction means.

7. The process according to claim 1 further comprising the steps of:

(e)(1) condensing said overhead vapor stream, thereby producing an overhead liquid stream, and (e)(2) feeding back a portion of said overhead liquid stream as reflux to said fractionation means.

* * * * *